(12) United States Patent
Joshi (10) Patent No.: US 9,240,630 B2
(45) Date of Patent: Jan. 19, 2016

(54) ANTENNA SHIELD FOR AN IMPLANTABLE MEDICAL DEVICE

(71) Applicant: CYBERONICS, INC., Houston, TX (US)

(72) Inventor: Himanshu Joshi, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 348 days.

(21) Appl. No.: 13/829,141

(22) Filed: Mar. 14, 2013

(65) Prior Publication Data

US 2013/0207863 A1 Aug. 15, 2013

Related U.S. Application Data

(63) Continuation-in-part of application No. 13/328,241, filed on Dec. 16, 2011, which is a continuation-in-part of application No. 13/098,279, filed on Apr. 29, 2011, now abandoned.

(51) Int. Cl.
| | |
|---|---|
| A61N 1/37 | (2006.01) |
| H01Q 1/42 | (2006.01) |
| A61N 1/372 | (2006.01) |
| H01Q 1/38 | (2006.01) |
| H01Q 13/10 | (2006.01) |
| H01Q 21/08 | (2006.01) |
| H01Q 21/20 | (2006.01) |
| H01Q 1/27 | (2006.01) |
| A61N 1/375 | (2006.01) |

(52) U.S. Cl.
CPC .............. *H01Q 1/42* (2013.01); *A61N 1/37229* (2013.01); *H01Q 1/273* (2013.01); *H01Q 1/38* (2013.01); *H01Q 13/10* (2013.01); *H01Q 21/08* (2013.01); *H01Q 21/205* (2013.01); *A61N 1/375* (2013.01)

(58) Field of Classification Search
CPC .................... A61N 1/37229; A61B 2018/183
See application file for complete search history.

(56) References Cited

U.S. PATENT DOCUMENTS

| | | |
|---|---|---|
| 4,030,480 A | 6/1977 | Meyer |
| 4,075,632 A | 2/1978 | Baldwin et al. |
| 4,127,110 A | 11/1978 | Bullara |
| 4,305,397 A | 12/1981 | Weisbrod et al. |
| 4,414,979 A | 11/1983 | Hirshorn et al. |
| 4,441,498 A | 4/1984 | Nordling |
| RE32,361 E | 2/1987 | Duggan |
| 4,800,899 A | 1/1989 | Elliott |
| 4,823,812 A | 4/1989 | Eshel et al. |
| 5,035,231 A | 7/1991 | Kubokawa et al. |

(Continued)

OTHER PUBLICATIONS

International Application No. PCT/US2012/032007, International Search Report and Written Opinion of the International Searching Authority dated Sep. 13, 2013, 13 pages.

*Primary Examiner* — Christopher D Koharski
*Assistant Examiner* — Natasha Patel (57) ABSTRACT

An implantable medical device includes a housing. An opening is present in the housing. The implantable medical device includes an antenna in the housing, where the antenna is located below the opening. The implantable medical device includes a cover coupled to edges of the housing defining the opening to close the opening. The cover enables passage of radio frequency signals at one or more communication frequencies to and from the antenna. The implantable medical device also includes an antenna shield positioned above the cover. The antenna shield reduces passage of radio frequency signals to and from at least a portion of the antenna during use.

20 Claims, 5 Drawing Sheets

(56) References Cited

U.S. PATENT DOCUMENTS

| | | |
|---|---|---|
| 5,050,605 A | 9/1991 | Eydelman et al. |
| 5,058,581 A | 10/1991 | Silvian |
| 5,109,853 A | 5/1992 | Taicher et al. |
| 5,117,825 A | 6/1992 | Grevious |
| 5,168,871 A | 12/1992 | Grevious |
| 5,246,000 A | 9/1993 | Ellis et al. |
| 5,313,953 A | 5/1994 | Yomtov et al. |
| 5,314,453 A | 5/1994 | Jeutter |
| 5,330,518 A | 7/1994 | Neilson et al. |
| 5,336,245 A | 8/1994 | Adams et al. |
| 5,350,411 A | 9/1994 | Ryan et al. |
| 5,373,852 A | 12/1994 | Harrison et al. |
| 5,375,596 A | 12/1994 | Twiss et al. |
| 5,383,912 A | 1/1995 | Cox et al. |
| 5,402,788 A | 4/1995 | Fujio et al. |
| 5,456,698 A | 10/1995 | Byland et al. |
| 5,494,030 A | 2/1996 | Swartz et al. |
| 5,558,618 A | 9/1996 | Maniglia |
| 5,562,714 A | 10/1996 | Grevious |
| 5,629,678 A | 5/1997 | Gargano et al. |
| 5,630,835 A | 5/1997 | Brownlee |
| 5,697,958 A | 12/1997 | Paul et al. |
| 5,720,770 A | 2/1998 | Nappholz et al. |
| 5,735,887 A | 4/1998 | Barreras, Sr. et al. |
| 5,766,232 A | 6/1998 | Grevious et al. |
| 5,782,891 A | 7/1998 | Hassler et al. |
| 5,788,692 A | 8/1998 | Campbell et al. |
| 5,800,494 A | 9/1998 | Campbell et al. |
| 5,840,148 A | 11/1998 | Campbell et al. |
| 5,861,019 A | 1/1999 | Sun et al. |
| 5,873,840 A | 2/1999 | Neff |
| 5,902,251 A | 5/1999 | vanHooydonk |
| 5,928,145 A | 7/1999 | Ocali et al. |
| 5,951,594 A | 9/1999 | Kerver |
| 5,963,132 A | 10/1999 | Yoakum |
| 5,967,986 A | 10/1999 | Cimochowski et al. |
| 6,009,350 A | 12/1999 | Renken |
| 6,009,878 A | 1/2000 | Weijand et al. |
| 6,041,256 A | 3/2000 | Michel |
| 6,073,050 A | 6/2000 | Griffith |
| 6,115,634 A | 9/2000 | Donders et al. |
| 6,161,049 A | 12/2000 | Rudie et al. |
| 6,167,312 A | 12/2000 | Goedeke |
| 6,169,925 B1 | 1/2001 | Villaseca et al. |
| 6,175,768 B1 | 1/2001 | Arndt et al. |
| 6,176,856 B1 | 1/2001 | Jandak et al. |
| 6,190,382 B1 | 2/2001 | Ormsby et al. |
| 6,192,279 B1 | 2/2001 | Barreras, Sr. et al. |
| 6,201,993 B1 | 3/2001 | Kruse et al. |
| 6,240,317 B1 | 5/2001 | Villaseca et al. |
| 6,261,247 B1 | 7/2001 | Ishikawa et al. |
| 6,275,737 B1 | 8/2001 | Mann |
| 6,277,113 B1 | 8/2001 | Berube |
| 6,308,101 B1 | 10/2001 | Faltys et al. |
| 6,308,102 B1 | 10/2001 | Sieracki et al. |
| 6,379,300 B1 | 4/2002 | Haubrich |
| 6,393,327 B1 | 5/2002 | Scribner |
| 6,398,710 B1 | 6/2002 | Ishikawa et al. |
| 6,456,256 B1 | 9/2002 | Amundson et al. |
| 6,463,329 B1 | 10/2002 | Goedeke |
| 6,477,425 B1 | 11/2002 | Nowick et al. |
| 6,485,462 B1 | 11/2002 | Kriesel |
| 6,505,072 B1 | 1/2003 | Linder et al. |
| 6,516,227 B1 | 2/2003 | Meadows et al. |
| 6,556,169 B1 | 4/2003 | Fukuura et al. |
| 6,561,975 B1 | 5/2003 | Pool et al. |
| 6,574,510 B2 | 6/2003 | Von Arx et al. |
| 6,610,054 B1 | 8/2003 | Edwards et al. |
| 6,614,406 B2 | 9/2003 | Amundson et al. |
| 6,631,290 B1 | 10/2003 | Guck et al. |
| 6,675,810 B2 | 1/2004 | Krag |
| 6,682,480 B1 | 1/2004 | Habib et al. |
| 6,708,065 B2 | 3/2004 | Von Arx et al. |
| 6,805,667 B2 | 10/2004 | Christopherson et al. |
| 6,894,616 B1 | 5/2005 | Forster |
| 6,922,591 B2 | 7/2005 | Single |
| 6,924,773 B1 | 8/2005 | Paratte |
| 7,016,733 B2 | 3/2006 | Dublin et al. |
| 7,042,357 B2 | 5/2006 | Girvin et al. |
| 7,043,307 B1 | 5/2006 | Zelickson et al. |
| 7,064,725 B2 | 6/2006 | Shtrikman et al. |
| 7,092,763 B1 | 8/2006 | Griffith et al. |
| 7,146,861 B1 | 12/2006 | Cook et al. |
| 7,149,578 B2 | 12/2006 | Edvardsson |
| 7,174,212 B1 | 2/2007 | Klehn et al. |
| 7,191,013 B1 | 3/2007 | Miranda et al. |
| 7,203,549 B2 | 4/2007 | Schommer et al. |
| 7,209,792 B1 | 4/2007 | Parramon et al. |
| 7,212,866 B1 | 5/2007 | Griffith |
| 7,235,096 B1 | 6/2007 | Van Tassel et al. |
| 7,281,314 B2 | 10/2007 | Hess et al. |
| 7,286,877 B2 | 10/2007 | Daum |
| 7,317,946 B2 | 1/2008 | Twetan et al. |
| 7,399,280 B2 | 7/2008 | Liu et al. |
| 7,429,255 B2 | 9/2008 | Thompson |
| 7,432,723 B2 | 10/2008 | Ellis et al. |
| 7,483,732 B2 | 1/2009 | Zhong et al. |
| 7,483,752 B2 | 1/2009 | Von Arx et al. |
| 7,554,493 B1 | 6/2009 | Rahman |
| 7,561,921 B2 | 7/2009 | Phillips et al. |
| 7,577,476 B2 | 8/2009 | Hochman et al. |
| 7,695,435 B2 | 4/2010 | Benson et al. |
| 7,729,766 B2 | 6/2010 | Toy et al. |
| 7,860,476 B1 | 12/2010 | Karr et al. |
| 7,904,167 B2 | 3/2011 | Klosterman et al. |
| 7,907,091 B2 | 3/2011 | Zhang |
| 7,983,760 B2 | 7/2011 | Ginggen et al. |
| 8,253,640 B2 | 8/2012 | Kitayoshi et al. |
| 8,332,037 B2 | 12/2012 | Imran |
| 8,442,643 B2 | 5/2013 | Toy et al. |
| 8,565,891 B2 | 10/2013 | Mumbru et al. |
| 8,599,086 B2 | 12/2013 | Wong et al. |
| 8,725,263 B2 | 5/2014 | Yamamoto et al. |
| 8,738,111 B2 | 5/2014 | Sweeney et al. |
| 2002/0095195 A1 | 7/2002 | Mass et al. |
| 2005/0113886 A1 | 5/2005 | Fischell et al. |
| 2005/0222633 A1* | 10/2005 | Edvardsson ............... 607/36 |
| 2006/0028784 A1 | 2/2006 | Brendel |
| 2006/0247712 A1 | 11/2006 | Fuller et al. |
| 2007/0043399 A1* | 2/2007 | Stevenson ............ H05K 9/0039 607/37 |
| 2007/0123949 A1 | 5/2007 | Dabney et al. |
| 2007/0273606 A1 | 11/2007 | Mak et al. |
| 2008/0033500 A1 | 2/2008 | Strother et al. |
| 2008/0091242 A1 | 4/2008 | Kamath et al. |
| 2008/0198082 A1 | 8/2008 | Soler Castany et al. |
| 2008/0316112 A1 | 12/2008 | Zhang |
| 2009/0228075 A1 | 9/2009 | Dion |
| 2009/0248112 A1 | 10/2009 | Mumbru et al. |
| 2010/0060431 A1 | 3/2010 | Stevenson et al. |
| 2010/0082080 A1* | 4/2010 | Mateychuk ............... 607/60 |
| 2010/0109966 A1 | 5/2010 | Mateychuk et al. |
| 2010/0114205 A1 | 5/2010 | Donofrio et al. |
| 2010/0114225 A1 | 5/2010 | Imran et al. |
| 2010/0149042 A1* | 6/2010 | Utsi .................. H01Q 1/273 343/700 MS |
| 2010/0161002 A1 | 6/2010 | Aghassian et al. |
| 2010/0168818 A1 | 7/2010 | Barror et al. |
| 2010/0194541 A1 | 8/2010 | Stevenson et al. |
| 2010/0321163 A1 | 12/2010 | Stevenson |
| 2011/0004076 A1 | 1/2011 | Janna et al. |
| 2012/0071942 A1 | 3/2012 | Kamath et al. |
| 2012/0276856 A1 | 11/2012 | Joshi et al. |
| 2012/0326886 A1* | 12/2012 | Herman et al. .......... 340/870.07 |
| 2013/0289666 A1 | 10/2013 | Johnson et al. |

\* cited by examiner

ANTENNA SHIELD FOR AN IMPLANTABLE MEDICAL DEVICE

CLAIM OF PRIORITY

This application is a continuation-in-part of and claims priority to U.S. patent application Ser. No. 13/328,241 filed on Dec. 16, 2011, which is a continuation-in-part of U.S. patent application Ser. No. 13/098,279 filed Apr. 29, 2011, both of which are herein incorporated by reference in their entireties.

FIELD OF THE DISCLOSURE

The present disclosure is generally related to an antenna shield for an implantable medical device.

BACKGROUND

An implantable medical device (IMD) may wirelessly communicate with an external device. Wireless communication for IMDs may be at MICS radio frequencies (i.e., medical implant communications service radio frequencies between 402 MHz and 405 MHz), at ISM radio frequencies (i.e., industrial, scientific, and medical radio frequencies), or at other radio frequencies. The IMD may be a nerve stimulator (e.g., a vagus nerve stimulator), a pacemaker or other heart stimulation device, or another type of medical device. Wireless communication may enable the IMD to receive parameters, instructions, data, or combinations thereof, that specify operating characteristics of the IMD. Wireless communication may also enable the IMD to send information to the external device. The information may include operating parameters of the IMD, operation data, physiological data, power source information, and other data.

Wireless communication with an IMD can be problematic. For example, when the IMD has a conductive housing, and a communication antenna is located within the conductive housing, signals may be blocked or attenuated by the housing.

SUMMARY

In a particular embodiment, an implantable medical device includes a housing. An opening is present in the housing. The implantable medical device includes an antenna in the housing, where the antenna is located below the opening. The implantable medical device includes a cover coupled to edges of the housing defining the opening to close the opening. The cover enables passage of radio frequency signals at one or more communication frequencies to and from the antenna. The implantable medical device also includes an antenna shield positioned above the cover. The antenna shield reduces passage of radio frequency signals to and from at least a portion of the antenna during use. In the description, the terms "above," "below," and similar terms used in association with a structural element are used to denote relative positions or orientations associated with another structural element and with reference to the orientations depicted in the figures.

In another particular embodiment, an implantable medical device includes a housing. An opening is present in the housing. The implantable medical device includes an antenna in the housing, where the antenna is located below the opening. The implantable medical device also includes a cover coupled to the housing to close the opening. The cover may include an antenna shield coupled to the cover, where the antenna shield is configured to provide radio frequency shielding to the antenna.

In another particular embodiment, an implantable medical device includes a housing. An opening is present in a first portion of the housing. The implantable medical device includes an antenna in the housing. The implantable medical device includes a cover coupled to the first portion to seal the opening. The cover enables passage of radio frequency signals at one or more communication frequencies to and from the antenna. The implantable medical device includes a header coupled to the housing over at least a portion of the cover. The implantable medical device also includes an antenna shield positioned in the header. The antenna shield reduces passage of radio frequency signals to and from at least a portion of the antenna during use.

DETAILED DESCRIPTION

Figure 1:
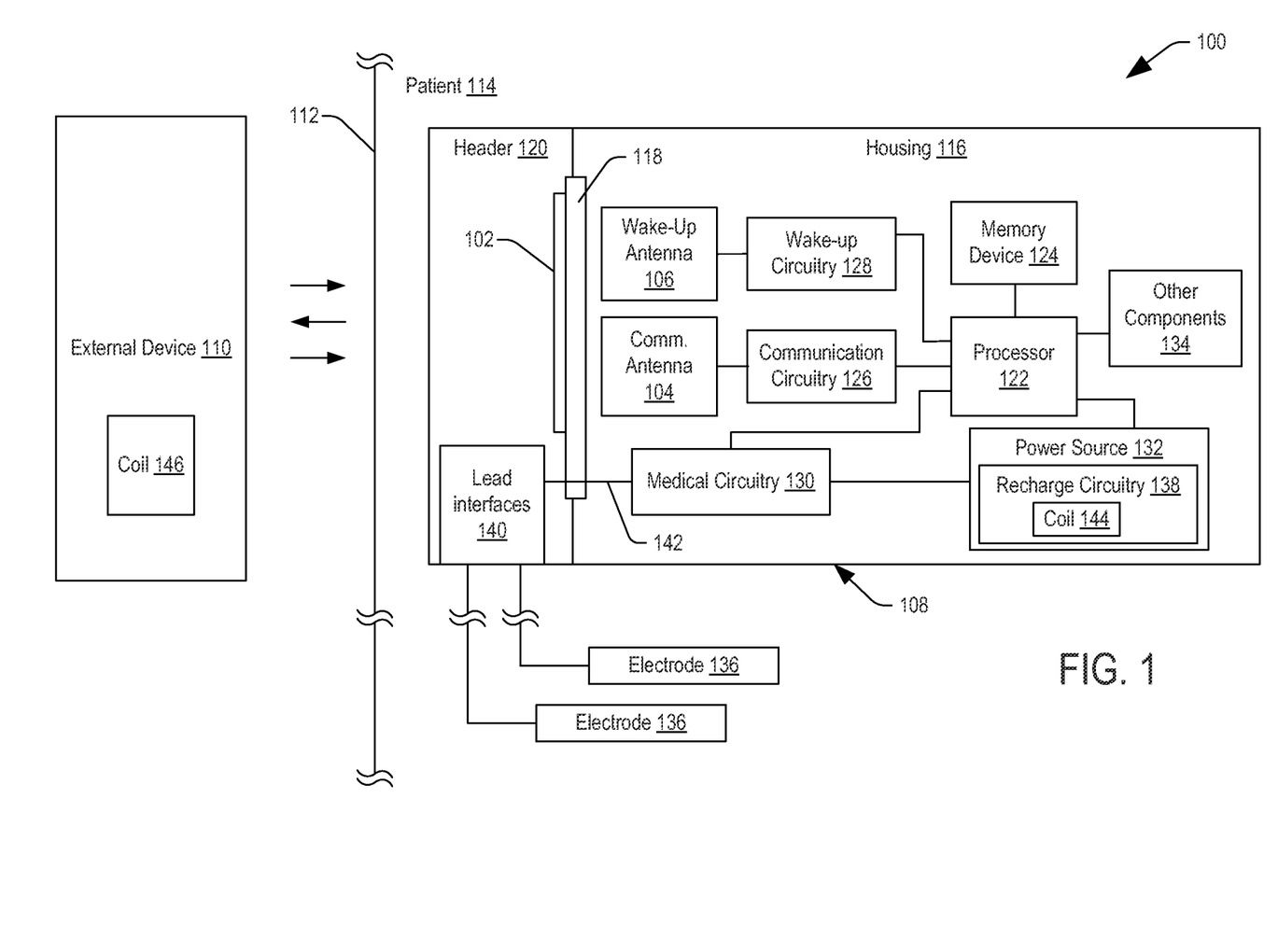
FIG. 1 is a block diagram of a first embodiment of a system that includes an implantable medical device and an external charging device.

FIG. 1 is a block diagram of a particular embodiment of a system 100 that includes an antenna shield 102 for one or more antennas 104, 106 of an implantable medical device (IMD) 108. The system 100 may include the IMD 108 and an external device 110. The IMD 108 may be positioned beneath skin 112 of a patient 114. The one or more antennas 104, 106 may receive first signals at one or more communication frequencies from the external device 110, transmit second signals at one or more communication frequencies to the external device 110, or both. The antenna shield 102 may improve the performance of one or both of the antennas 104, 106 by attenuating low frequency signals to a greater extent than signals at the one or more communication frequencies.

The IMD 108 may include a housing 116, a cover 118, the antenna shield 102, and a header 120. The housing 116 may be a metallic housing made of, for example, titanium, a titanium alloy, or another biocompatible metal. The housing 116 may be assembled from two or more pieces. For example, the housing 116 may be formed from a bottom piece and a top piece that are joined together. The pieces of the housing 116 may be joined together by one or more welds, by one or more press fit connections, by fasteners (e.g., screws, rivets, snaps, etc.), by adhesive, by other connection systems, or by combinations thereof. Components 104, 106, 122-134 of the IMD 108 may be positioned in the housing 116 before the pieces of the housing 116 are joined together.

The components 104, 106, 122-134 of the IMD 108 may include, but are not limited to, a processor 122, a memory device 124, a communication antenna 104, a wake-up antenna 106, communication circuitry 126, wake-up circuitry 128, medical circuitry 130, a power source 132, and other components 134. Some or all of the components 104, 106, 122-134 may be positioned on, or may be part of, one or more circuit boards coupled to the housing 116. The components 104, 106, 122-134 may be hermetically sealed within the housing 116 when the IMD 108 is assembled.

The processor 122 may control operation of the IMD 108. The processor 122 may be communicatively coupled to the memory device 124. The memory device 124 may include one or more devices and may include internal memory of the processor 122. The memory device 124 may include (e.g., store) instructions executable by the processor 122 to implement functionality of the IMD 108. The memory device 124 may store parameters and data used by the processor 122 to determine characteristics (e.g., amplitude, polarity, frequency, pulse width, pulse period, duty cycle, charge balancing, signal duration, etc.) of treatment signals to be applied to the patient 114 by the IMD 108. The parameters and data may also indicate when the treatment signals are to be applied to the patient 114 via one or more electrodes 136 (e.g., at scheduled times or in response to one or more conditions). The memory device 124 may also, or in the alternative, store data identifying applied treatment signals, diagnostic information associated with the IMD 108, and sensor data from one or more sensors coupled to the IMD 108. The data may be received from one or more of the electrodes 136, from one or more heart beat sensors, from one or more temperature sensors, from other sensors, or combinations thereof. For example, the electrodes or one or more sensors may be implanted within or coupled to tissue of the patient 114 and may transmit data, or signals, to the IMD 108 via wired or wireless connections.

The processor 122 may be coupled to the communication circuitry 126. The communication circuitry 126 may be coupled to the communication antenna 104. The communication circuitry 126 may include matching components to improve performance of the communication antenna 104 at communication frequencies used by the IMD 108 to transmit and receive data via the communication antenna 104. The communication circuitry 126 may enable the processor 122 to send information via the communication antenna 104 to the external device 110. The information may include data stored by the memory device 124. For example, the information may include data corresponding to operation of the IMD 108, diagnostic information for the IMD 108, data corresponding to current conditions of the IMD 108, or combinations thereof. The communication circuitry 126 may also, or in the alternative, enable the processor 122 to receive, via the communication antenna 104, parameters, data, instructions, or combinations thereof from the external device 110. In an embodiment, the communication antenna 104 may be a planar antenna (e.g., a slot antenna with a conductive layer on a surface of a circuit board). In other embodiments, the communication antenna 104 may be another type of antenna. For example, the communication antenna 104 may be, but is not limited to, a dipole antenna, a monopole antenna, a serpentine antenna, a patch antenna, a plane-inverted-F antenna, a helical antenna, a fractal antenna, a loop antenna, or an antenna with another form factor.

The processor 122 may be coupled to the wake-up circuitry 128. The wake-up circuitry 128 may be coupled to the wake-up antenna 106. The wake-up circuitry 128 may include matching components to improve performance of the wake-up antenna 106 at wake-up signal frequencies. The wake-up signal frequencies may be different than frequencies used to communicate via the communication antenna 104. For example, in an illustrative embodiment, the wake-up signal frequencies may be at about 2.45 GHz while the frequencies used to communicate via the communication antenna 104 may be at about 400 MHz. The external device 110 may send a wake-up signal to the IMD 108 when a communication session is to be established between the IMD 108 and the external device 110. The wake-up circuitry 128 may send signals received via the wake-up antenna 106 at the wake-up signal frequencies to the processor 122.

When the processor 122 determines that the signals received from the wake-up circuitry 128 include the wake-up signal, the processor 122 may cause the communication circuitry 126, components capable of entering a sleep state (e.g., recharge circuitry 138 of the power source 132), or both, to transition from a sleep state to an active state where the components capable of entering the sleep state are ready to communicate, perform functions, or both. The communication circuitry 126 and the other components of the IMD 108 capable of entering a sleep state may enter the sleep state after particular periods of inactivity to conserve power or for other reasons. In response to the wake-up signal, the processor 122 may cause the communication circuitry 126 to send an acknowledgement signal to the external device 110 that informs the external device 110 that the IMD 108 is ready to communicate with the external device 110.

In an embodiment, the wake-up antenna 106 may be a surface-mountable chip antenna and may be housed in a small form-factor ceramic or polymer package. In other embodiments, the wake-up antenna 106 may be another type of antenna. In some embodiments, the IMD 108 may not include the wake-up antenna 106 and the wake-up circuitry 128 may be coupled to the communication antenna 104.

The processor 122 may be coupled to the medical circuitry 130. The medical circuitry 130 may be coupled to one or more lead interfaces 140 in the header 120 via feedthroughs 142. The medical circuitry 130 may include therapy circuitry to provide treatment signals to the patient 114 via one or more of the feedthroughs 142. The medical circuitry 130 may also, or in the alternative, include sensing circuitry to receive physiological data associated with the patient 114 from one or more sensors coupled to the IMD 108. The one or more sensors may include, but are not limited to, one or more of the electrodes 136, one or more temperature sensors, a heart rate sensor, an oximeter, an accelerometer, a blood pressure monitor, another type of sensor, or combinations thereof.

The processor 122 may be coupled to the power source 132. The power source 132 may also be coupled to one or more of the memory device 124, the communication circuitry 126, the wake-up circuitry 128, the medical circuitry 130, and the other components 134. The power source 132 may include one or more batteries, capacitors, other charge storage devices, or combinations thereof, to power the IMD 108 and components thereof. Batteries of the power source 132 may include rechargeable batteries, non-rechargeable batteries, or combinations thereof. The power source 132 may include or be coupled to the recharge circuitry 138 that enables the power source 132 to be recharged. In an embodiment, the recharge circuitry 138 may include a coil 144. A current may be induced in the coil 144 by a primary current flowing through a coil 146 of the external device 110. The induced current in the coil 144 may be used to recharge the power source 132.

The processor 122 may receive status information from the recharge circuitry 138 during recharging of the power source 132. The status information may include charge frequency information to facilitate determination of a resonant frequency for charging, charge completion information, other information, or combinations thereof. The external device 110 may receive charge information from the processor 122 via the communication circuitry 126 and the communication antenna 104. The charge information may include status information received by the processor 122 from the recharge circuitry 138, information determined by the processor 122 based on the status information, information received from the other components 134 (e.g., temperature information of the power source 132, the housing 116, or both), commands (e.g., a reduce recharge rate command, a stop recharge command, etc.), or combinations thereof. The commands may be sent based on status of a recharge process. For example, the reduce recharge rate command may be sent when a temperature increase rate of the IMD 108 exceeds a threshold. In response to the reduce recharge rate command, the external device 110 may adjust one or more properties of a charging signal applied to the coil 146 or may initiate periodic charging of the power source 132 followed by periods of time when no charging occurs until the power source 132 is recharged to a threshold state. As another example, the stop recharge command may be sent to the external device 110 when the power source 132 is recharged to the threshold state. In response to the stop recharge command, the external device 110 may cease applying the charging signal to the coil 146.

The processor 122, the components 102, 104, 124-132 of the IMD 108, and the housing 116 may be coupled to one or more of the other components 134. The other components 134 may include but are not limited to temperature sensors, other sensors, flexible electrical connectors, mounts, and so forth.

The housing 116 may have an opening that is closed, or otherwise filled by a cover 118. The cover 118 may be sealed to the housing 116 to substantially close the opening. The cover 118 may be part of a feedthrough and may provide one or more openings for feedthroughs 142 to pass through. The cover 118 may be a dielectric material (e.g., a ceramic, a polymer, or other dielectric material) that allows passage of radio frequency signals to and from the antennas 104, 106. The opening, the cover 118, and the position of the antennas 104, 106 in the housing 116 may facilitate communication between the external device 110 and the IMD 108.

The feedthroughs 142 may pass from the medical circuitry 130 in the housing 116 through openings in the cover 118 to one or more lead interfaces 140 in the header 120. The feedthroughs 142 may be sealed to the cover 118. In an embodiment, the feedthroughs 142 for a particular lead interface of the lead interfaces 140 may include a feed and a return. In another embodiment, a particular lead interface may be connected to a single feedthrough 142. The single feedthrough 142 may be a feed for a treatment signal. A return path for the treatment signal may be through the patient 114 to the housing 116.

The header 120 may be coupled to the housing 116. The header 120 may be formed of one or more biocompatible polymers. The header 120 may be coupled to the housing 116 by a press fit, by one or more connectors (e.g., screws, rivets, snaps, etc.), by an adhesive (e.g., an epoxy), by another type of polymer to metal connection, or by combinations thereof. One or more of the lead interfaces 140 may be positioned in or attached to the header 120. One or more of the electrodes 136, other treatment devices, sensors, or combinations thereof, may be coupled to the lead interfaces 140.

The antenna shield 102 may be positioned between the header 120 and the cover 118. In some embodiments, the antenna shield 102 may be coupled (e.g., adhered or otherwise fastened) to the cover 118, may be formed on the cover 118 (e.g., printed or deposited on the cover 118), may be attached to or deposited on a bottom surface of the header 120, may be positioned in the header 120, or may be attached to or deposited on a top surface of the header 120. The antenna shield 102 may provide radio frequency shielding to the communication antenna 104. The radio frequency shielding may reduce passage of at least some (e.g., attenuate) radio frequency signals to and from the communication antenna 104. For example, the antenna shield 102 may attenuate low frequency signals more than higher frequency signals (e.g., signals at one or more communication frequencies).

Figure 4:
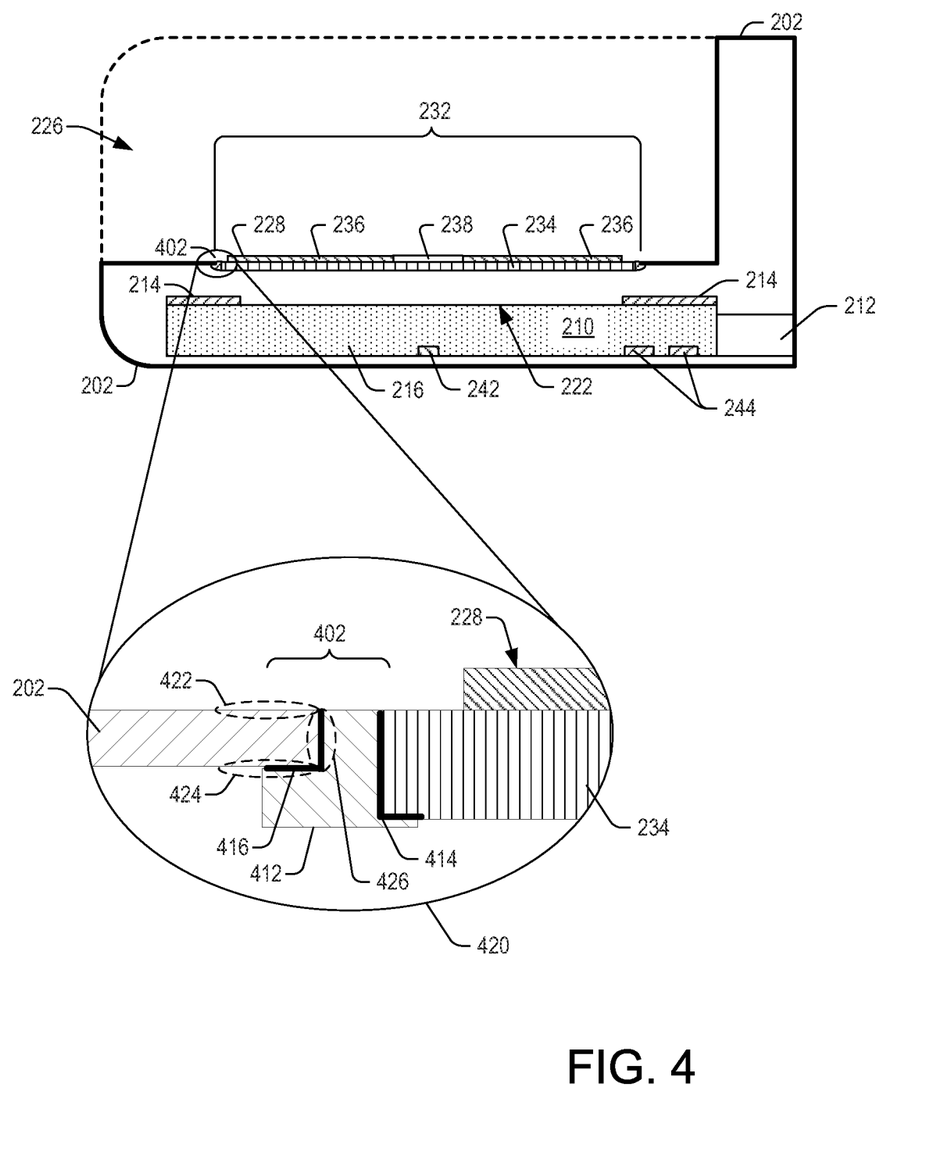
FIG. 4 depicts a cross-sectional view of an embodiment of an implantable medical device taken substantially along the plane indicated by section lines A-A of FIG. 2.

Table 1 shows simulation data that enables comparison of an IMD without an antenna shield to an embodiment of the IMD 108 that includes the antenna shield 102 coupled to the cover 118 above the communication antenna 104. In both cases, the communication antenna is located within the housing of the IMD. The antenna shield 102 was simulated as a conductive layer (i.e., copper) with an opening (e.g., an unshielded portion) in the conductive layer positioned directly above a portion of the communication antenna 104 (e.g., similar to the layout of an antenna shield 228 with an unshielded portion 238 positioned directly above an antenna 222 as depicted in FIG. 4). Table 2 shows simulation data that enables comparison of an IMD without an antenna shield to an embodiment of the IMD 108 that includes an antenna shield positioned about 1 millimeter within the header 120 (e.g., similar to the antenna shield 604 positioned in the header 600 depicted in FIG. 6) and directly above a portion of the communication antenna 104.

TABLE 1

| Communication Frequency (MHz) | Peak Gain Of Antenna For IMD Without Shield (dB) | Peak Gain Of Antenna For IMD With Shield (dB) | Attenuation Due To Antenna Shield (dB) |
|---|---|---|---|
| 10 | −117.5 | −121.6 | 4.1 |
| 64 | −93.4 | −96.3 | 2.9 |
| 128 | −69.2 | −71.1 | 1.9 |
| 400 | −31.2 | −32.9 | 1.7 |

TABLE 2

| Communication Frequency (MHz) | Peak Gain Of Antenna For IMD Without Shield (dB) | Peak Gain Of Antenna For IMD With Shield (dB) | Attenuation Due To Antenna Shield (dB) |
|---|---|---|---|
| 10 | −117.5 | −131.9 | 14.4 |
| 64 | −93.4 | −95.3 | 1.9 |
| 128 | −69.2 | −71.0 | 1.8 |
| 400 | −31.2 | −32.4 | 1.2 |

Tables 1 and 2 show that attenuation due to presence of the antenna shield 102 above the communication antenna 104 is reduced at higher frequencies as compared to lower frequencies. The antenna shield 102 may improve the performance of the communication antenna 106 by attenuating low frequency signals to a greater extent than signals at communication frequencies (e.g., frequencies at or near to 400 MHz). Further, the antenna shield 102 causes little attenuation at the communication frequencies.

The external device 110 may communicate with the IMD 108. The external device 110 may provide data to the IMD 108, may receive information from the IMD 108, or both. In some embodiments, the coil 146 of the external device 110 may be used to recharge the power source 132 of the IMD 108. In other embodiments, the external device 110 may not include the coil 146.

Figure 2:
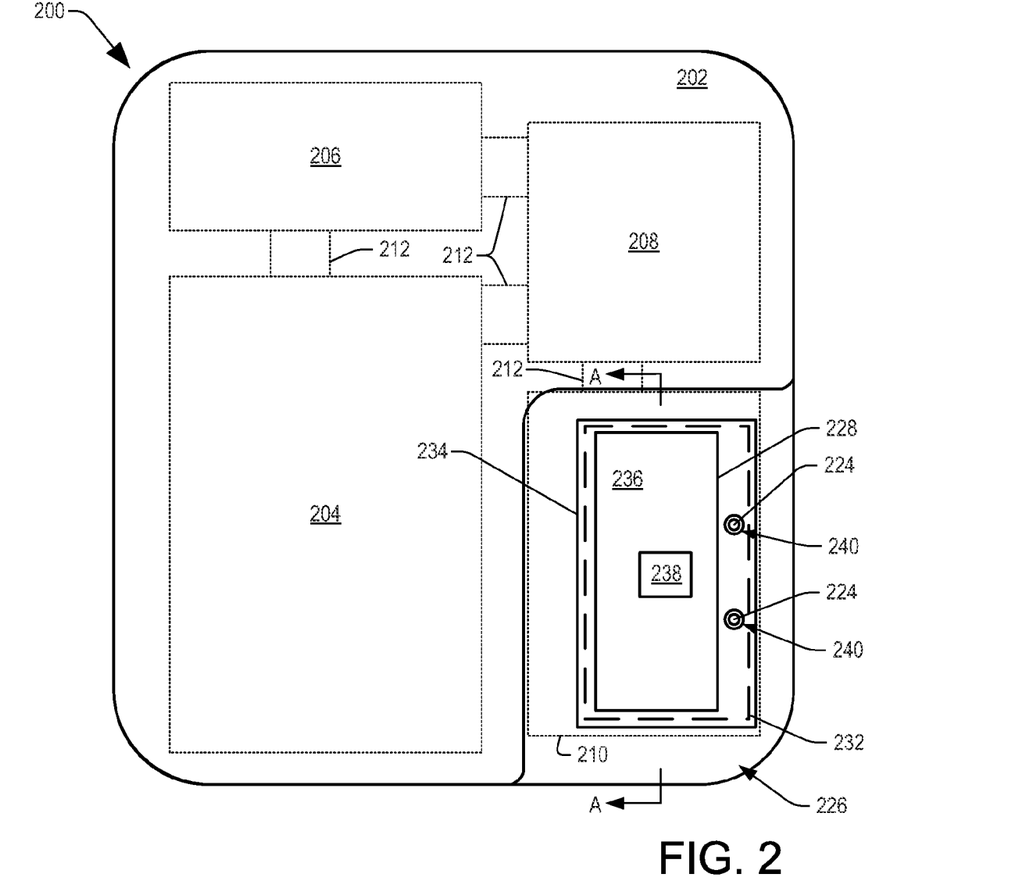
FIG. 2 is a schematic illustration of a top view of a second embodiment of an implantable medical device without a header and lead interfaces.

FIG. 2 is a schematic illustration of a top view of an IMD 200 before a header and lead interfaces are coupled to the IMD 200. In the view depicted in FIG. 2, components 204-212 of the IMD 200 are internally positioned in a housing 202 (as indicated by dotted lines). The components 204-212 may include a power source 204, functional circuitry 206 (e.g., medical circuitry, a processor, a memory device, other components, or combinations thereof), communication circuitry 208, an output circuit board 210, and connectors 212. The communication circuitry 208 may include a receiver, a transmitter, a coder/decoder (CODEC), wake-up circuitry, other components, or combinations thereof that facilitate communication between an external device (e.g., an external device that is outside of a patient) and the IMD 200 when the IMD 200 is implanted in a patient. The connectors 212 may electrically and communicatively couple the components 204-210 of the IMD 200 to each other.

Figure 3:
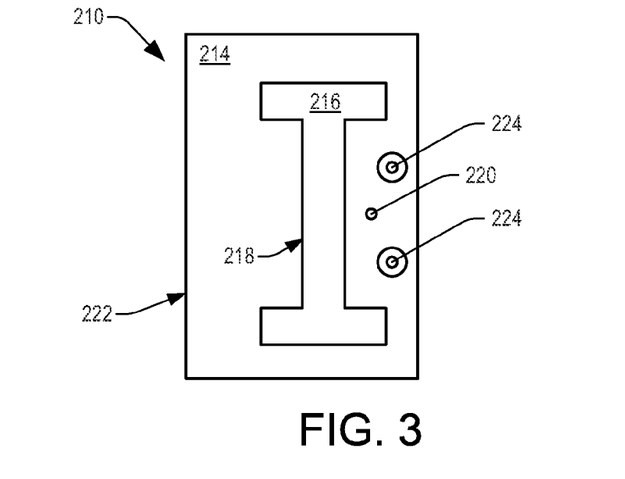
FIG. 3 is a top view of an embodiment of an output circuit board.

FIG. 3 depicts a top view of an embodiment of the output circuit board 210 of FIG. 2. The output circuit board 210 may include a conductive layer 214 (e.g., a copper layer) and a non-conductive layer 216 defined by one or more openings 218 in the conductive layer 214. The non-conductive layer 216 may include dielectric material of the output circuit board 210. An antenna feed 220 may be electrically coupled (e.g., from below) to the conductive layer 214. The conductive layer 214, the one or more openings 218 in the conductive layer 214, and the antenna feed 220 may form an antenna 222 that enables communication with an external device. Edges of the conductive layer 214, including edges of the conductive layer 214 defined by the one or more openings 218 may form radiating/receiving elements of the antenna 222. The output circuit board 210 may also include feedthroughs 224 that extend out of the output circuit board 210. The feedthroughs 224 may be electrically isolated from the conductive layer 214.

As depicted in FIG. 2 (and in FIG. 4), the housing 202 may include a recessed portion 226. A cover 234 may be coupled to edges of an opening 232 in the recessed portion 226 of the housing 202 above the output circuit board 210. An antenna shield 228 may be coupled to the cover 234 and may be a radio frequency shield for the antenna 222 (depicted in FIG. 3). In FIG. 2, edges that define the opening 232 are represented by dashed lines. In the description, the terms "above," "below," and similar terms used in association with a structural element are used to denote relative positions or orientations associated with another structural element and with reference to the orientations depicted in the figures. In an embodiment, the antenna shield 228 may include one or more unshielded portions 238 and one or more shielded portions 236. The shielded portions 236 of the antenna shield 228 may include a metal layer adhered, deposited, or otherwise attached to a ceramic sheet (i.e., the cover 234). The antenna shield 228 may include one or more unshielded portions 238 that do not include a metal layer. The metal layer forming the shielded portions 236 of the antenna shield 228 may be copper, gold, or another metal.

The shielded portions 236 of the antenna shield 228 may be positioned above the output circuit board 210 to shield at least a portion of the antenna 222 (shown in FIG. 3) of the output circuit board 210. One or more of the shielded portions 236 may extend over a portion of one or more radiating/receiving elements of the antenna 222 (shown in FIG. 3) of the output circuit board 210. In some embodiments, antenna shield 228 may include one or more of the unshielded portions 238 interspersed with the one or more conductive sections of the shielded portions 236. The one or more unshielded portions 238 may be a single unshielded portion 238 as depicted in FIG. 2 or a plurality of unshielded portions (e.g., two or more spaced apart unshielded portions formed in the metal layer of the one or more shielded portions 236 or one or more arrayed patterns of unshielded portions, such as a grid or mesh, formed in the metal layer). When the unshielded portions 238 of the antenna shield 228 are positioned directly above non-conductive layers 216 of the antenna 222 (shown in FIG. 3), the shielded portions 236 of the antenna shield 228 may extend over more than half, more than 70%, or a larger portion of an area of the non-conductive layers 216 of the antenna. In some embodiments, the antenna shield 228 may be a uniform metal layer with no unshielded portions 238.

Feedthroughs 224 from the output circuit board 210 may pass through feedthrough openings 240 in the cover 234. The feedthroughs 224 may be coupled to lead assemblies of the IMD 200 during assembly of the IMD 200. The feedthroughs 224 may be electrically connected to the functional circuitry 206 by one or more of the connectors 212, by feedthrough feed lines in the output circuit board 210, or by combinations thereof. In other embodiments, only one feedthrough 224 or more than two feedthroughs 224 may pass through the cover 234, through another portion of the housing 202, or combinations thereof to accommodate electrodes, sensors, or other devices coupled to the IMD 200.

FIG. 4 depicts a cross-sectional view taken substantially along a cutting plane indicated by section lines A-A shown in FIG. 2. The output circuit board 210 may be positioned in the housing 202 below the opening 232 in the housing 202. The cover 234 may be sealed to the housing 202 in the recessed potion 226. One or more shielded portions 236 of the antenna shield 228 may be coupled to (e.g., deposited, printed, or adhered) the cover 234. The unshielded portion 238 of the antenna shield 228 may be positioned directly above the opening 232 in the housing 202 and directly above a portion of the antenna 222. The output circuit board 210 may include the conductive layer 214, the non-conductive layer 216, an antenna feed line 242, and feedthrough feed lines 244. The unshielded portion 238 of the antenna shield 228 may be positioned directly above a portion of the conductive layer 214 of the output circuit board 210 and directly above a portion of the non-conductive layer 216 of the output circuit board 210 that form portions of the antenna 222. One or more connectors 212 may be coupled to the output circuit board 210. The antenna shield 228 may be made of biocompatible materials or may be coated with a biocompatible material to inhibit interaction with a patient should a connection between a header that is secured to the housing 202 in the recessed portion 226 fail.

In some embodiments, as illustrated in an exploded view 420, an electrically conductive seal 402 may include a metal flange 412 brazed or otherwise attached to the outer perimeter of the cover 234. A first filler material 414 may be used to attach/seal the metal flange 412 to the cover 234. The cover 234 may be a ceramic based material, the metal flange 412 may include titanium, and the first filler material 414 may include gold. Various other materials may be used to provide a dielectric cover with a flange. The antenna shield 228 may be deposited on the cover 234. The conductive material for the antenna shield 228 may include gold or copper and may be a very thin layer (the layers of FIG. 4 are draw for illustrative purposes and may not be to scale). For example, the thickness of the antenna shield 228 may be on the order of several to hundreds of microns. In some embodiments, the antenna shield 228 may have a thickness of 2-20 microns. The metal flange 412 may be configured to engage, and be sealed to, edges of the housing 202 defining the opening 232. The edges of the housing 202 around the opening 232 may include a top surface edge 422, a bottom surface edge 424, an inner perimeter surface edge 426, or any combination thereof. In some embodiments, the metal flange 412 may engage the bottom surface edge 424 and the inner perimeter surface edge 426 of the opening 232. The metal flange 412 may be laser welded, brazed, or otherwise sealed to the edges of the housing 202 as illustrated by a joint 416 formed between the housing 202 and the metal flange 412. Positioning the cover 234 so that the metal flange 412 engages the bottom surface edge 424 and the inner perimeter surface edge 426 of the opening 232, as illustrate in the exploded view 420, may allow the cover 234 to be substantially flush with the outside of the housing 202 in the recessed portion 226.

Figure 5:
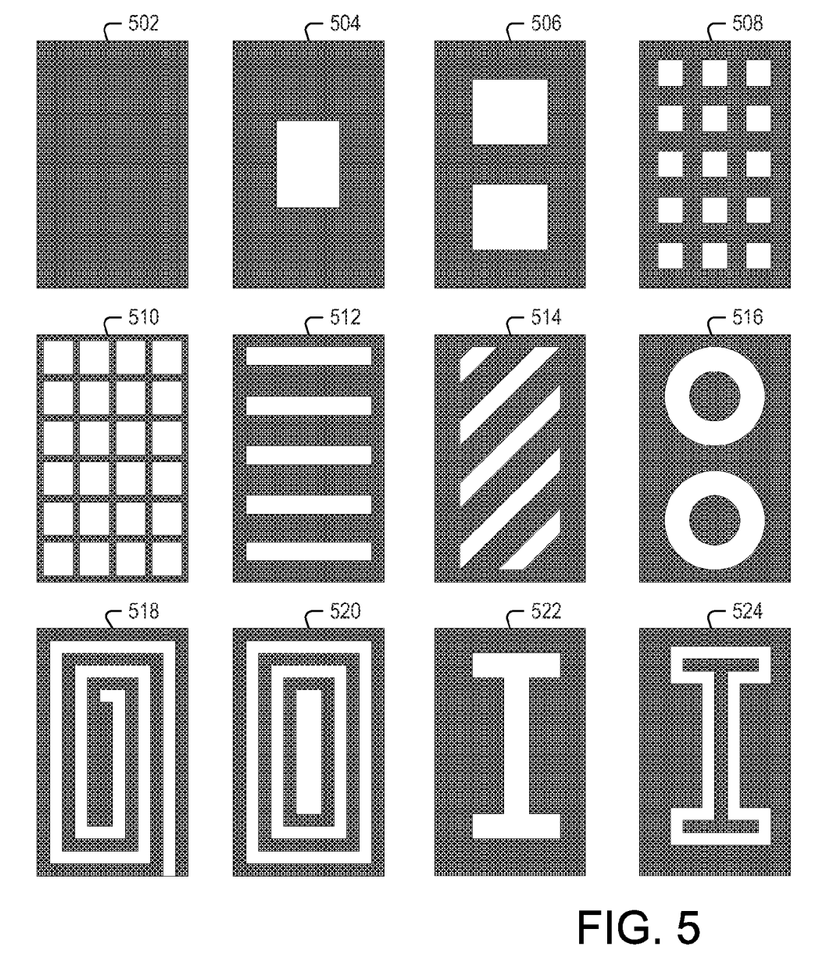
FIG. 5 depicts a top view of various embodiments of an antenna shield.

FIG. 5 depicts a top view of various antenna shield configurations. Antenna shield 502 is a solid conductive layer with no cutouts. Antenna shield 504 includes a conductive layer with a single cutout similar to the antenna shield 228 of FIG. 2. The cutout illustrated is a rectangular shape, however, any shape may be used for the cutout (e.g., circle, triangle, square, diamond, ellipse, rhombus, or any other polygon shape). Multiple cutouts may be used. For example, antenna shield 506 includes a conductive layer with two cutouts, antenna shield 508 includes more than two cutouts (e.g., 15 cutouts), and antenna shield 510 includes more than two cutouts where the metal between cutouts is more narrow than the metal between cutouts in antenna shields 506 and 508. Antenna shields 508 and 510 form mesh patterns and are meant to be illustrative only. Various other mesh patterns could be used. For example, the cutouts may be other shapes and sizes, need not be uniform is size, shape, and/or position, may include more or less cutouts, and may have different spacing between cutouts. Antenna shield 512 includes a conductive layer with elongated rectangle cutouts that may be oriented either horizontally (as shown) or vertically. Antenna shield 514 may include a conductive layer with elongated cutouts oriented at one or more angles with respect to horizontal or vertical orientations.

Antenna shield 516 includes a conductive layer with two ring shape cutouts. One, or more than two ring shape cutouts may be used. Antenna shield 518 includes a spiral configuration in the conductive layer. Antenna shield 520 includes multiple conductive loops or rings of diminishing size. The rings or loops may be concentric. Antenna shield 522 includes a conductive layer with a dog bone shaped cutout. The dog bone shaped cutout may be used to conform to the dog bone shape of the underlying slot antenna. The cutout of the antenna shield may conform to the shape of the underlying antenna, whatever that shape may be. In some embodiments, the cutout may track or be positioned over the edges of the underlying antenna. For example, antenna shield 524 may have cutouts that are positioned over the edges of the underlying dog bone shaped slot antenna. The dimensions of the one or more cutouts in an antenna shield may depend upon the one or more communication frequencies used by the antenna of the device, the one or more frequencies desired to be attenuated, the dimensions/shape of the underlying antenna, a distance between the underlying antenna and the antenna shield, the number of and position of the cutouts, or a combination thereof.

In some embodiments, the antenna shield may be coupled to a cover (e.g., dielectric material) that seals an opening in a housing of an IMD. In some embodiments, the antenna shield may be coupled to a header positioned in a recessed portion of an IMD so that the antenna shield is positioned over at least a portion of an antenna within the housing of the IMD. When the antenna shield is coupled to the header, the antenna shield may be coupled to, or deposited on, a bottom surface of the header; may be in the header; or may be coupled to a top surface of the header. When the antenna shield is coupled to the top surface or the bottom surface of the header, the antenna shield may be a biocompatible material or may be coated with a biocompatible material. In some embodiments, the antenna shield may include one or more unshielded portions (e.g., one or more openings or one or more regions of non-conductive material interspersed in a region of conductive material). In some embodiments, more than one antenna shield may be used. For example, a first antenna shield may be coupled to the cover and a second antenna shield may be provided within the header above the first antenna shield.

Figure 6:
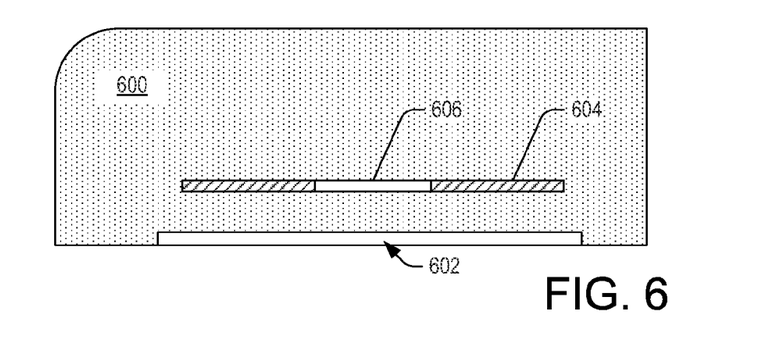
FIG. 6 depicts a cross-sectional view of an embodiment of a header with an antenna shield positioned in the header.

FIG. 6 depicts a cross-sectional view of the antenna shield 604 positioned in a header 600. The antenna shield 604 may include at least one unshielded portion 606 (e.g., a cutout). The header 600 may be shaped to fit in a recessed portion of a housing of an IMD (e.g., the recessed portion 226 depicted in FIGS. 2 and 4). The header 600 may include a recessed volume 602 to accommodate any portion of a seal and the cover (e.g., a ceramic sheet) that are above flush with the surface of the housing. The recessed volume 602 may not be present when the seal for the cover and an upper surface of the cover are below or flush with the surface of the housing. In some embodiments, the antenna shield may be positioned within the header 600 approximately 1 millimeter above the cover of the IMD. The distance between the antenna shield and the cover may depend upon the one or more communication frequencies used by the antenna of the device, the one or more frequencies desired to be attenuated, the dimensions/shape of the underlying antenna, a distance between the underlying antenna and the cover, the number of and position of the cutouts, or a combination thereof.

When the antenna shield 604 is positioned in the header 600 over a planar antenna having at least one unshielded portion 606 in a conductive layer of the antenna (such as the antenna 222 depicted in FIG. 3), the antenna shield 604 may extend over most or all of an area defined by the one or more openings in the conductive layer of the antenna. For example, the antenna shield 604 may extend over half of the area defined by the one or more openings, over 75% of the area defined by the one or more openings, or all of the area defined by the one or more openings.

Various embodiments herein disclose implantable medical devices that include antenna shields. The antenna shield of an implantable medical device may provide shielding for one or more antennas used by the medical device to communicate with an external device. The antenna shield may improve the performance of the one or more antennas by attenuating low frequency signals (e.g., noise) to a greater extent than communication signals at one or more communication frequencies (e.g., higher frequency signals).

Figure 7:
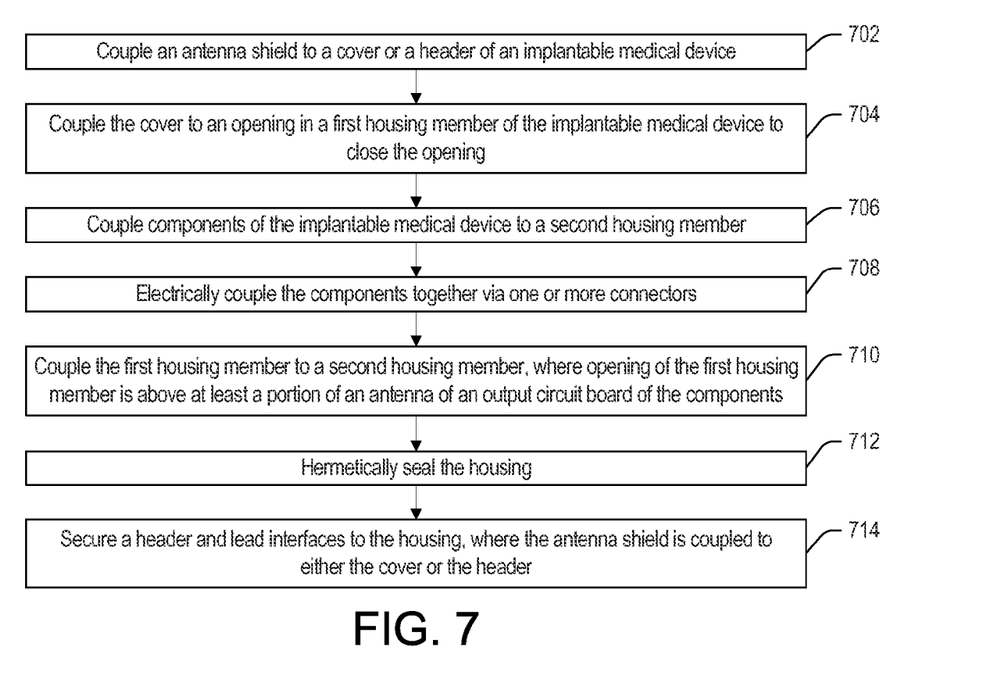
FIG. 7 depicts a flow chart of an embodiment of a method of manufacturing an implantable medical device.

FIG. 7 is a flow chart of a particular embodiment of a method of manufacturing an implantable medical device (IMD) with an antenna shield. The method may be performed to manufacture the IMD 108 of FIG. 1, to manufacture the IMD 200 depicted in FIG. 2 with a header and lead interfaces, or to manufacture an IMD with the antenna shield coupled to the header of the IMD. An antenna shield may be coupled to a cover or a header of an implantable medical device, at 702. The antenna shield may include one or more unshielded portions or may include no unshielded portions. In some embodiments, the antenna shield may be adhered to the cover, or may be otherwise attached to the cover before or after the cover is coupled to the housing. In some embodiments, the antenna shield may be a layer deposited or printed on the cover. In some embodiments, the antenna shield may be coupled to the header of the IMD. The antenna shield may be positioned in the header as the header is formed, may be fixed or deposited on a bottom surface of the header, or may be fixed or deposited to a top surface of the header.

At 704, the cover may be coupled to an opening in a first housing member of the implantable medical device to close the opening. In some embodiments, the cover is coupled and sealed to the first housing member prior to coupling the first housing member to a second housing member. Feedthroughs that are electrically coupled to the medical circuitry of the IMD may be positioned through openings in the cover. In some embodiments, the cover may be a sheet of dielectric material, such as a ceramic.

At 706, components of the IMD may be coupled to the second housing member. The components may include a power source, functional circuitry (e.g., medical circuitry, a processor, a memory device, other components, or combinations thereof), communication circuitry, an output circuit board, other discrete devices or circuits, or a combination thereof. The output circuit board may include a communication antenna to receive signals that represent first data from an external device, to transmit signals that represent second data to the external device, or both. In some embodiments, the output circuit board may include a wake-up antenna that receives a wake-up signal from the external device. One or more connectors may electrically couple the components together, at 708. The one or more connectors may include, but are not limited to circuit boards, wires, flexible connectors that attach to mating sockets, solder, or combinations thereof. In some embodiments, one or more of the components may be coupled to the first housing member.

At 710, the second housing member may be coupled to the first housing member, where the opening in the first housing member may be positioned above at least a portion of the first antenna of the output circuit board when the second member is coupled to the first member. Positioners of the first housing member and the second housing member may guide proper alignment and positioning of the second housing member relative to the first housing member. The positioners may include pins, slots, grooves, keyways, or other elements that facilitate assembly, alignment, or both, of the first housing member relative to the second housing member.

The housing may be hermetically sealed, at 712. Hermetically sealing the housing may include sealing the first housing member to the second housing member, sealing the cover to the first surface, filling openings for the feedthroughs with sealant, sealing other openings in the housing, or combinations thereof.

At 714, the header and lead interfaces may be secured to the housing, where the antenna shield is coupled to either the cover or the header. The lead interfaces may be integral components of the header or separate components. The lead interfaces may be electrically coupled to the feedthroughs. When the antenna shield is coupled to the header, securing the header and the lead interfaces to the housing may position the antenna shield above at least a portion of the first antenna.

Figure 8:
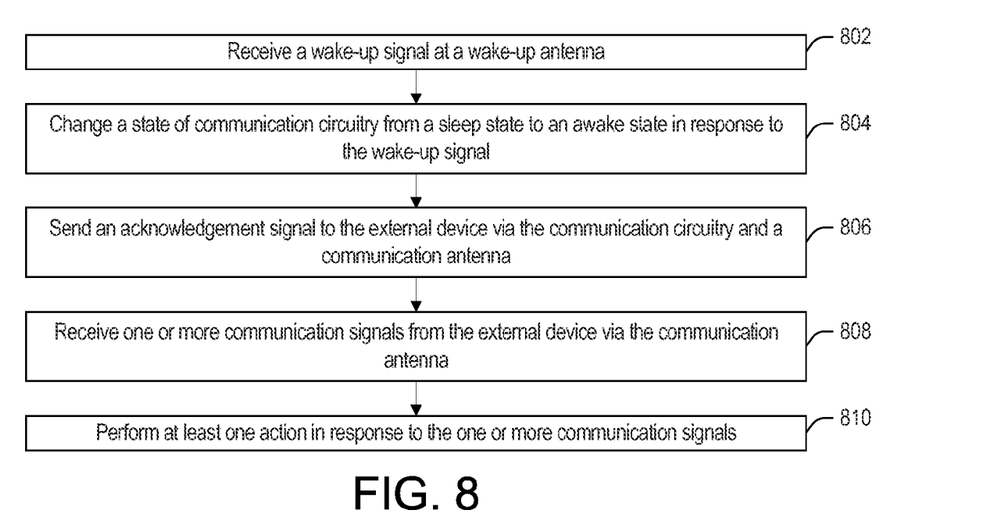
FIG. 8 depicts a flow chart of an embodiment of a method of communicating with an implantable medical device.

FIG. 8 is a flow chart of a particular embodiment of a method of communicating with an implantable medical device (IMD). The method may be performed by the IMD 108 of FIG. 1 or the IMD 200 of FIG. 2 (when the IMD 200 includes a header and lead interfaces; when the IMD 200 is coupled to one or more electrodes, one or more other devices, or both; and when the IMD 200 is implanted in a patient). An external device may send a wake-up signal to the IMD. At 802, the IMD may receive the wake-up signal at a wake-up antenna.

The wake-up antenna may be a component of the IMD hermetically sealed within a housing of the IMD. Other components of the IMD that are hermetically sealed within the housing may include, but are not limited to, a power source, functional circuitry (e.g., medical circuitry, a processor, a memory device, other components, or combinations thereof), communication circuitry, wake-up circuitry, an output circuit board, and connectors. The output circuit board may include the wake-up antenna, a communication antenna, or both. In some embodiments, the wake-up antenna and the communication antenna are two separate antennas. In other embodiments, the wake-up antenna and the communication antenna are a single antenna. A portion of the output circuit board may be located beneath an opening in the housing that is sealed by a cover. A portion of the communication antenna may be located directly below the cover. An antenna shield may be positioned directly above at least a portion of the communication antenna that is located directly below the cover. The antenna shield may be an integral component of the cover, may be coupled to the cover, may be coupled to a bottom surface of a header that is positioned over the cover and secured to the housing, may be positioned in the header, may be coupled to a top surface of the header, or may be a combination thereof. The antenna shield may improve the performance of the communication antenna by attenuating low frequency signals received by the communication antenna to a greater extent than signals at communication frequencies (e.g., frequencies at or near 400 MHz) while still having relatively small attenuation due to the presence of the antenna shield at the communication frequencies. The low frequency signals may include, for example, noise.

In response to the wake-up signal, the IMD may change a state of communication circuitry from a sleep state, in which the communication circuitry is unpowered, to an awake state, in which power is supplied to the communication circuitry, at 804. The communication circuitry may be placed in the sleep state when the communication circuitry is inactive for a particular period of time or by a particular command received from the external device. When the communication circuitry is in the awake state, the communication circuitry may be able to receive first communication signals from the external device, may be able to send second communication signals to the external device, or both.

The IMD may send an acknowledgement signal to the external device via the communication circuitry and the communication antenna, at 806. The acknowledgement signal may inform the external device that a communication session with the IMD is established.

The external device may send one or more communication signals to the IMD. The one or more communication signals may include commands for the IMD (e.g., requests for information, such as power source status, operation data, other information, or combinations thereof), may include operation instructions and operational data for the IMD (e.g., operation instructions and operation data that changes what treatment signals are sent by the IMD to the patient, when the treatment signals are sent to the patient, or both), other information, or combinations thereof The IMD may receive the one or more communication signals via the communication antenna, at 808. The IMD may perform at least one action in response to the one or more communication signals, at 810.

Although the description above contains many specificities, these specificities illustrate some of the exemplary embodiments of this disclosure and should not be construed as limiting the scope of the disclosure. The scope of this disclosure should be determined by the claims, their legal equivalents and other embodiments which may become apparent to those skilled in the art. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. In the description, the terms "above," "below," and similar terms used in association with a structural element are used to denote relative positions or orientations associated with another structural element and with reference to the orientations depicted in the figures. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods and programs of the present disclosure. However, describing the disclosure with drawings should not be construed as imposing on the disclosure any limitations that may be present in the drawings. The present disclosure describes methods, systems and program products on any machine-readable media for accomplishing its operations. The embodiments of the present disclosure may be implemented using a computer processor, or by a special purpose computer processor incorporated for this or another purpose or by a hardwired system.

As noted above, embodiments within the scope of the present disclosure include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can include RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media (e.g., a computer-readable storage device). Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

It should be noted that although the flowcharts provided herein show a specific order of method steps, it is understood that the order of these steps may differ from what is depicted. Also, two or more steps may be performed concurrently or with partial concurrence. It is understood that all such variations are within the scope of the disclosure. Likewise, software and web implementations of the present disclosure could be accomplished with standard programming techniques with rule based logic and other logic to accomplish the various steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to a particular application.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An implantable medical device comprising:
a housing, wherein an opening is present in the housing;
an antenna in the housing, wherein the antenna is located below the opening;
a cover coupled to edges of the housing defining the opening to close the opening, wherein the cover enables passage of radio frequency signals at one or more communication frequencies to and from the antenna; and an antenna shield positioned above the cover, wherein the antenna shield reduces passage of radio frequency signals to and from at least a portion of the antenna during use.

2. The implantable medical device of claim 1, further comprising a header coupled to the housing, wherein the cover is covered by the header.

3. The implantable medical device of claim 2, wherein the antenna shield is positioned in the header.

4. The implantable medical device of claim 2, wherein the antenna shield is coupled to the header.

5. The implantable medical device of claim 1, wherein the antenna shield is coupled to the cover.

6. The implantable medical device of claim 1, wherein the antenna shield includes at least one unshielded portion.

7. The implantable medical device of claim 1, wherein at least one radiating/receiving element of the antenna is located directly below the cover.

8. The implantable medical device of claim 1, wherein the antenna shield attenuates signals at frequencies lower than the one or more communication frequencies to a greater extent than the antenna shield attenuates signals at the one or more communication frequencies.

9. An implantable medical device comprising:
a housing, wherein an opening is present in the housing;
an antenna in the housing, wherein the antenna is located below the opening; and
a cover coupled to the housing to close the opening, the cover including an antenna shield coupled to the cover, the antenna shield configured to provide radio frequency shielding to the antenna during use.

10. The implantable medical device of claim 9, wherein the antenna shield includes a conductive layer deposited on a top surface of the cover.

11. The implantable medical device of claim 10, wherein the antenna shield comprises one or more openings in the conductive layer.

12. The implantable medical device of claim 11, wherein at least one opening of the one or more openings is positioned directly above one or more radiating/receiving elements of the antenna.

13. The implantable medical device of claim 9, wherein the antenna comprises a planar antenna with one or more slots, and wherein conductive portions of the antenna shield are located directly above more than half of an area of a non-conductive portion of the antenna defined by the one or more slots.

14. The implantable medical device of claim 9, wherein the antenna shield attenuates signals at frequencies lower than one or more communication frequencies to a greater extent than the antenna shield attenuates signals at the one or more communication frequencies.

15. An implantable medical device comprising:
a housing, wherein an opening is present in a first portion of the housing;
an antenna in the housing;
a cover coupled to the first portion to seal the opening, wherein the cover enables passage of radio frequency signals at one or more communication frequencies to and from the antenna;
a header coupled to the housing over at least a portion of the cover; and
an antenna shield positioned in the header, wherein the antenna shield reduces passage of radio frequency signals to and from at least a portion of the antenna during use.

16. The implantable medical device of claim 15, wherein the antenna shield comprises one or more unshielded portions.

17. The implantable medical device of claim 15, wherein the cover comprises a ceramic sheet.

18. The implantable medical device of claim 15, wherein the antenna comprises a planar antenna including one or more conductive layers and one or more non-conductive layers defined by one or more openings in the one or more conductive layers, and wherein the antenna shield extends over more than half of an area defined by the one or more openings.

19. The implantable medical device of claim 15, wherein at least a portion of one or more radiating/receiving elements of the antenna is located directly below the antenna shield.

20. The implantable medical device of claim 15, wherein the antenna shield attenuates signals at frequencies lower than the one or more communication frequencies to a greater extent than the antenna shield attenuates signals at the one or more communication frequencies.

\* \* \* \* \*